United States Patent
Whitaker et al.

(10) Patent No.: US 11,246,606 B2
(45) Date of Patent: Feb. 15, 2022

(54) DRILL BIT

(71) Applicant: BIOMET 3I, LLC, Palm Beach Gardens, FL (US)

(72) Inventors: Weston Whitaker, Jupiter, FL (US); Kaushal Kumar, Palm Beach Gardens, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 16/990,704

(22) Filed: Aug. 11, 2020

(65) Prior Publication Data

US 2021/0045752 A1 Feb. 18, 2021

Related U.S. Application Data

(60) Provisional application No. 62/885,535, filed on Aug. 12, 2019.

(51) Int. Cl.
A61B 17/16 (2006.01)
(52) U.S. Cl.
CPC ...... A61B 17/1615 (2013.01); A61B 17/1622 (2013.01)
(58) Field of Classification Search
CPC . A61B 17/16; A61B 17/1613; A61B 17/1615; A61B 17/1617; A61B 17/1622; A61B 17/1624; A61B 17/1655; A61B 17/1662; A61B 17/1673; A61C 3/02
See application file for complete search history.

(56) References Cited

U.S. PATENT DOCUMENTS

| | | | |
|---|---|---|---|
| 5,330,480 A | 7/1994 | Meloul et al. | |
| 5,575,650 A * | 11/1996 | Niznick | A61C 8/0089 408/224 |
| 6,641,395 B2 * | 11/2003 | Kumar | A61B 17/1615 433/165 |
| 7,402,040 B2 * | 7/2008 | Turri | A61B 17/1624 433/165 |
| 7,665,989 B2 * | 2/2010 | Brajnovic | B23B 51/10 433/165 |
| 9,326,778 B2 * | 5/2016 | Huwais | A61C 8/0089 |
| 9,826,990 B2 * | 11/2017 | Ahn | A61B 17/1673 |
| 10,912,572 B2 * | 2/2021 | Kunz | A61C 8/0089 |
| 10,987,111 B2 * | 4/2021 | Feldmann | A61B 17/1615 |

(Continued)

FOREIGN PATENT DOCUMENTS

JP 2009131634 A * 6/2009 ........... A61C 8/0089

OTHER PUBLICATIONS

"European Application Serial No. 20190765.6, Extended European Search Report dated Dec. 3, 2020", 7 pgs.

*Primary Examiner* — Eric S Gibson
(74) *Attorney, Agent, or Firm* — Schwegman Lundberg & Woessner, P.A.

(57) ABSTRACT

Drill bits for cutting bones adjacent to soft tissue are disclosed. According to one example, the drill bit includes a working portion having a top cutting surface including a first top cutting surface and a second top cutting surface. The second stop cutting surface has an angle with respect to a line perpendicular to the longitudinal axis of the drill bit that is less than an angle with respect to a line perpendicular to the longitudinal axis of the drill bit of the first top cutting surface.

20 Claims, 8 Drawing Sheets

(56) References Cited

U.S. PATENT DOCUMENTS

| | | | |
|---|---|---|---|
| 2002/0031745 A1* | 3/2002 | Kumar | A61C 8/0089 433/165 |
| 2005/0118550 A1* | 6/2005 | Turri | A61C 1/148 433/65 |
| 2006/0210949 A1* | 9/2006 | Stoop | A61C 8/0089 433/165 |
| 2009/0142731 A1* | 6/2009 | Kim | A61C 3/02 433/165 |
| 2009/0228011 A1 | 9/2009 | Agbodoe et al. | |
| 2010/0145341 A1* | 6/2010 | Ranck | A61B 17/1615 606/80 |
| 2013/0046308 A1 | 2/2013 | Heo | |
| 2013/0218160 A1* | 8/2013 | Bjorn | A61B 17/1679 606/80 |
| 2013/0224683 A1* | 8/2013 | Zacharia | A61C 1/0069 433/165 |
| 2014/0065573 A1* | 3/2014 | Wang | A61C 8/0089 433/166 |
| 2014/0113245 A1* | 4/2014 | Heo | A61C 1/084 433/75 |
| 2015/0094725 A1* | 4/2015 | Ahn | A61B 17/1688 606/80 |
| 2015/0150565 A1* | 6/2015 | Huwais | A61B 17/1615 606/84 |
| 2015/0282895 A1* | 10/2015 | Theorin | A61B 5/4509 433/165 |
| 2015/0342617 A1* | 12/2015 | Kunz | A61C 1/14 433/75 |
| 2018/0161124 A1* | 6/2018 | Huwais | A61B 90/03 |
| 2019/0029695 A1* | 1/2019 | Huwais | A61B 17/1673 |
| 2019/0029696 A1* | 1/2019 | Feldmann | A61B 17/1615 |
| 2019/0038385 A1* | 2/2019 | Burke | A61B 17/1615 |
| 2019/0142438 A1* | 5/2019 | Skajster | A61B 17/1671 606/79 |
| 2019/0321144 A1* | 10/2019 | Kim | A61C 8/0089 |
| 2020/0029978 A1* | 1/2020 | Boukhris | A61B 17/162 |
| 2020/0246116 A1* | 8/2020 | Jacoby | A61C 8/0089 |
| 2021/0045752 A1* | 2/2021 | Whitaker | A61C 3/02 |

* cited by examiner

DRILL BIT

CLAIM OF PRIORITY

This application claims the benefit of priority to U.S. Provisional Application No. 62/885,535, filed Aug. 12, 2019, titled "DRILL BIT"; which is hereby incorporated herein by reference in its entirety.

FIELD OF THE DISCLOSURE

The present invention relates to a drill bit, and more particularly, relates to a dental drill bits for use in drilling bones that have soft tissue opposing the bone being drilled.

BACKGROUND

The human skeleton consists of many kinds of bones including, upper and lower jawbones and spine or skull, that can have, for example, various thicknesses and surrounding materials. Depending on the location, thickness, and surrounding materials such as membrane linings and other soft tissues, drilling the bone can present various challenges.

In case of some dental patients, the structure of the oral cavity makes it difficult to perform the implant surgery, so that the dental surgery becomes complicated, or some dentists often decline to give such a patient medical treatment. In particular, the surgeon has difficulty in performing the implant installation in the case where a small amount of bone remains in the posterior area near the maxillary sinus. In this case, the maxillary sinus membrane can be elevated to secure a space, a bone graft is placed in the secured space, and a dental implant can be embedded in this space. This method is classified into a vertical approach and a lateral approach.

Many tools such as drills are used for various drill procedures. Conventional drill bits can be applied to cases in that has sufficient bone depth or in locations where other important anatomy such as membranes, nerves or cells are not present. However, in cases where the bone depth is light, bone thickness is thin, or other important parts such as the membranes, nerves or cells are present, even the most skillful person needs to drill such that no damage is done to these other important parts. While these conventional drill bits may easily penetrate the bone, the tips of the drill blades can damage the membrane by tearing or rolling when the tip of the drill contacts the membrane.

SUMMARY

This disclosure pertains generally to drill bits that facilitate precisely and quickly drilling bones without damages surrounding soft tissue, such as soft tissue opposing the bone being drilled. The drill bit disclosed herein can drill through bone without perforating membrane linings or other soft tissues on the other side of the bone that is being drilled. Previous approaches have utilized a drill bit that needed a pilot drill or bur to initiate the cut in the bone. Further, these previous approaches relied on the drill bit to leave bone chips (formed from the drilling) between the drill and the soft tissue to form a "bone disk" that would protect, e.g., the sinus membrane or other soft tissue, from rupturing.

However, the present inventors have recognized, among other things, that these bone chips may not always form and/or stay behind forming the "bone disk" between the drill and the soft tissue and lead to the perforation or damage of the soft tissues opposing the drill. Perforation of the membrane or damage to soft tissue during drilling is not desirable and further procedures and time to the patient are required to correct the perforation or damage and increase the time for the patient to receive their dental implant.

The present disclosure provides a drill bit that can be used in areas that have soft tissues opposing the bone being drilled. Examples can include, but are not limited to, the maxillary sinus area, in the skull, spine, and other bones adjacent to soft tissue. Accordingly, there is a need to develop a bone drill that can be used without the use of a pilot drill as well as protecting the soft tissue opposing the bone being drilled.

The present invention solves the above-mentioned problems of the conventional art. The drill bit includes a working portion that includes at least one channel, wherein the channel defines a cutting blade portion including a top cutting surface including a first top cutting surface and a second top cutting surface. The first top cutting surface is a top of the drill that has an angle with respect to a line perpendicular to a longitudinal axis of the drill bit that is greater than angle of the second cutting surface. The angles of the first cutting surface and the second cutting surface are such that a separate pilot drill is not needed and the drill bit can initiate the pilot hole n its own. However, the angles and axial heights of the first cutting surface and the second cutting surface are not so sharp as to puncture a membranous lining or other soft tissue opposing the drill. Thus, the drill bit of the present application can minimize the probability of puncturing or otherwise damaging soft tissue such as membranes, even if a bone disk is not created to separate the drill from the membrane. The drill bit also includes benefits such as channels to retain bone chips to use as autograft, a blocking portion that can stop the drilling action at a predetermined depth and has a standard attachment shaft that will allow the drill bit to be used in existing tool handpieces.

To better illustrate the embodiments disclosed, a non-limiting list of examples is provided here:

Example 1 includes a surgical drill bit can optionally comprise a mounting portion extending from a first end to a second end, the mounting portion configured to mount to a tool; and a working portion adjacent the first end of the mounting portion, the working portion configured for cutting a hole in a bone, the working portion including: a body portion extending from a distal end to a proximal end, the body portion including a top surface and a side surface; a blocking portion formed at the proximal end of the body portion and having a first diameter greater than a maximum diameter of the body portion; at least one channel formed in a longitudinal direction of the working portion, the at least one channel extending from the top surface through the blocking portion, wherein the at least one channel defines, along the body portion, a cutting blade portion configured to cut the bone upon rotation of the surgical drill bit, the cutting blade portion including: a first top cutting surface having a first angle relative a longitudinal axis of the body portion; and a second top cutting surface having a second angle relative the longitudinal axis, the second angle less than the first angle.

In Example 2, the Example 1 can optionally be configured such that the first angle is between about 15 degrees to about 45 degrees with respect to a line perpendicular to the longitudinal axis In Example 3, any one of Examples 1-2, can optionally be configured such that the first angle is about 25 degrees with respect to a line perpendicular to the longitudinal axis.

In Example 4, any one of Examples 1-3, can optionally be configured such that the second angle is between 10 degrees to about 25 degrees with respect to a line perpendicular to the longitudinal axis.

In Example 5, any one of Examples 1-4, can optionally be configured such that the second angle is 25 degrees with respect to a line perpendicular to the longitudinal axis.

In Example 6, any one of Examples 1-5, can optionally be configured such that the at least one channel is a plurality of channels each defining, along the body portion, the cutting blade portion.

In Example 7, the Example 6, can optionally be configured such that the cutting blade portion of each channel of the plurality of channels meet at a merging point on the longitudinal axis.

In Example 8, any one of Examples 1-7, can optionally be configured such that along a profile of the working portion, the first top cutting surface changes to the second top cutting surface at a transition point.

In Example 9, the Example 8, can optionally be configured such that the transition point is halfway between a total height along the profile of the first top cutting surface and the second top cutting surface.

In Example 10, any one of Examples 1-9, can optionally be configured such that the first top cutting surface extends from a merging point to a proximal end, wherein the second top cutting surface extends from a distal end to a cutting corner, and wherein the proximal end of the first top cutting surface is positioned proximally to the distal end of the second top cutting surface.

In Example 11, a surgical drill bit can optionally comprise a mounting portion extending from a first end to a second end, the mouthing portion configured to mount to a tool; and a working portion adjacent the first end of the mounting portion, the working portion configured for cutting a hole in a bone, the working portion including: a body portion extending from a distal end to a proximal end, the body portion including a top surface and a side surface; and at least one channel extending through the body portion, wherein the at least one channel defines, along the body portion, a cutting blade portion, including: a first top cutting surface having a first angle relative a longitudinal axis of the body portion; and a second top cutting surface having a second angle relative the longitudinal axis that is greater than 10 degrees with respect to a line perpendicular to the longitudinal axis of the body portion, wherein the second angle is less than the first angle.

In Example 12, the Example 11, can optionally be configured such that a total axial height of the first top cutting surface and the second top cutting surface is about 1.0 millimeter (mm).

In Example 13, any one of Examples 11-12, can optionally be configured such that a height of the first top cutting surface is one of: equal to a height of the second top cutting surface and less than the height of the second top cutting surface.

In Example 14, any one of the Examples 11-13, can optionally be configured such that the first angle is between about 15 degrees to about 45 degrees with respect to a line perpendicular to the longitudinal axis In Example 15, any one of the Examples 11-14, can optionally be configured such that the second angle is between 10 degrees to about 25 degrees with respect to the line perpendicular to the longitudinal axis.

In Example 16, any one of Examples 11-15, can optionally be configured such that the at least one channel is a plurality of channels each defining, along the body portion, the cutting blade portion.

In Example 17, the Example 16, can optionally be configured such that the cutting blade portion of each channel of the plurality of channels meet at a merging point on the longitudinal axis.

In Example 18, A surgical drill bit can optionally comprise a mounting portion extending from a first end to a second end, the mouthing portion configured to mount to a tool; and a working portion adjacent the first end of the mounting portion, the working portion configured for cutting a hole in a bone, the working portion including: a body portion extending from a distal end to a proximal end, the body portion including a top surface and a side surface; and at least one channel extending through the body portion, wherein the at least one channel defines, along the body portion, a cutting blade portion, including: a first top cutting surface having a first angle relative a longitudinal axis of the body portion; and a second top cutting surface having a second angle relative the longitudinal axis, the second angle less than the first angle, wherein an axial height of the first top cutting surface is equal to or less than an axial height of the second top cutting surface.

In Example 19, the Example 18, can optionally be configured such that the first angle is between about 15 degrees to about 45 degrees with respect to a line perpendicular to the longitudinal axis.

In Example 20, any one of the Examples 18-19, can optionally be configured such that the second angle is between 10 degrees to about 25 degrees with respect to the line perpendicular to the longitudinal axis.

In Example 21, the system of any one or any combination of Examples 1-20 can optionally be configured such that all elements or options recited are available to use or select from.

These and other examples and features of the present apparatuses, and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses, systems and methods.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

The present disclosure provides a drill bit that can be used in areas that have soft tissues opposing the bone being drilled. For example, drills used in sinus lift procedures can benefit from the drill bit disclosed as the drilling is being done to bone that is adjacent to the sinus membranes.

Figure 1:
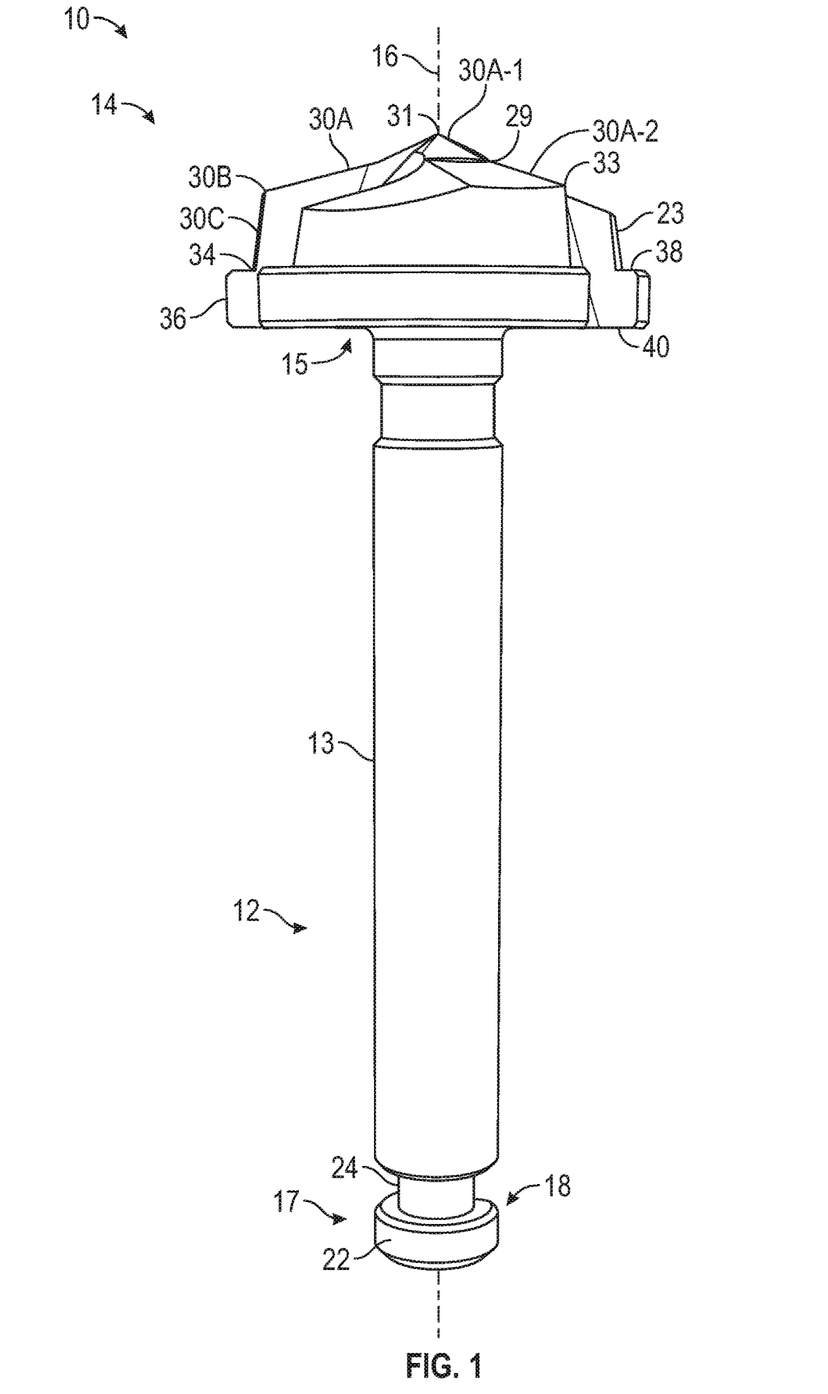
FIG. 1 illustrates a side view of a drill bit, according to one example of the present disclosure.
Figure 2:
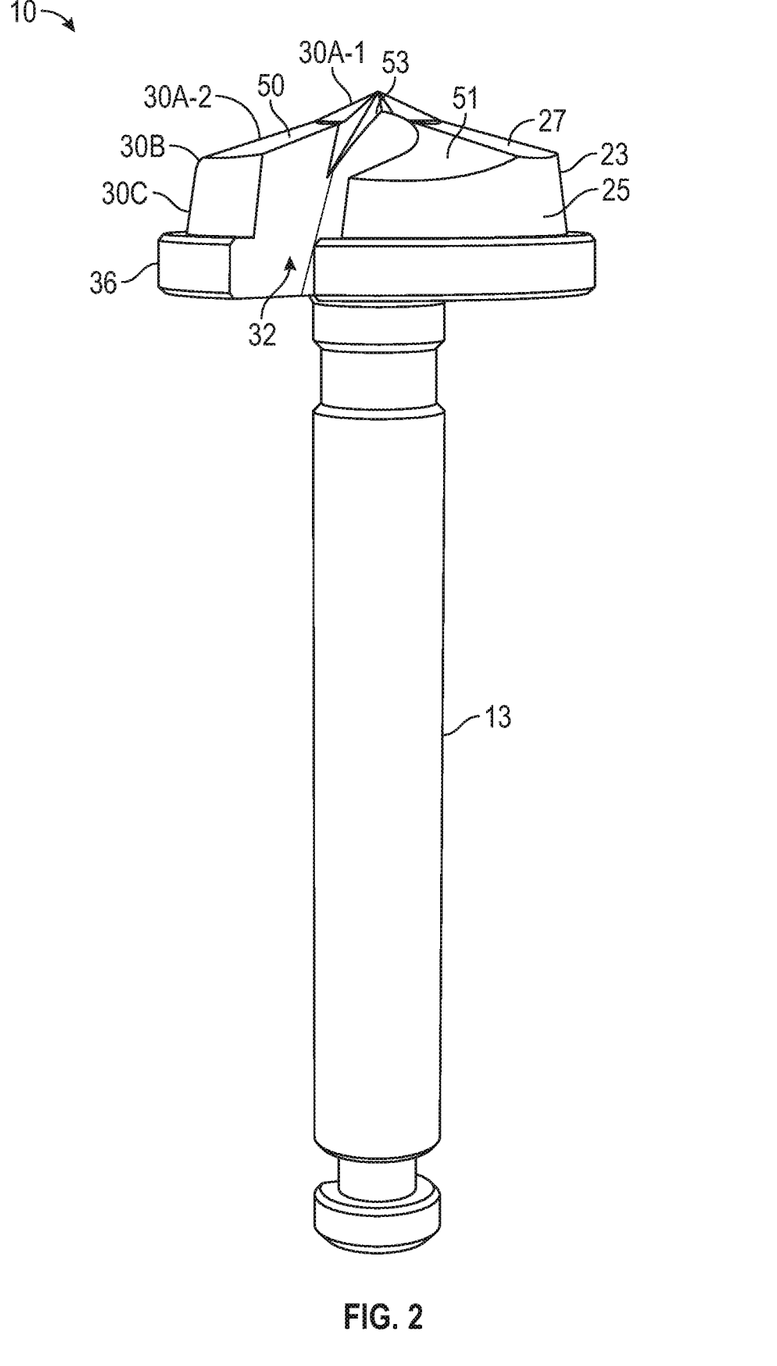
FIG. 2 illustrates a side view of a drill bit in FIG. 1 rotated about a longitudinal axis.
Figure 3:
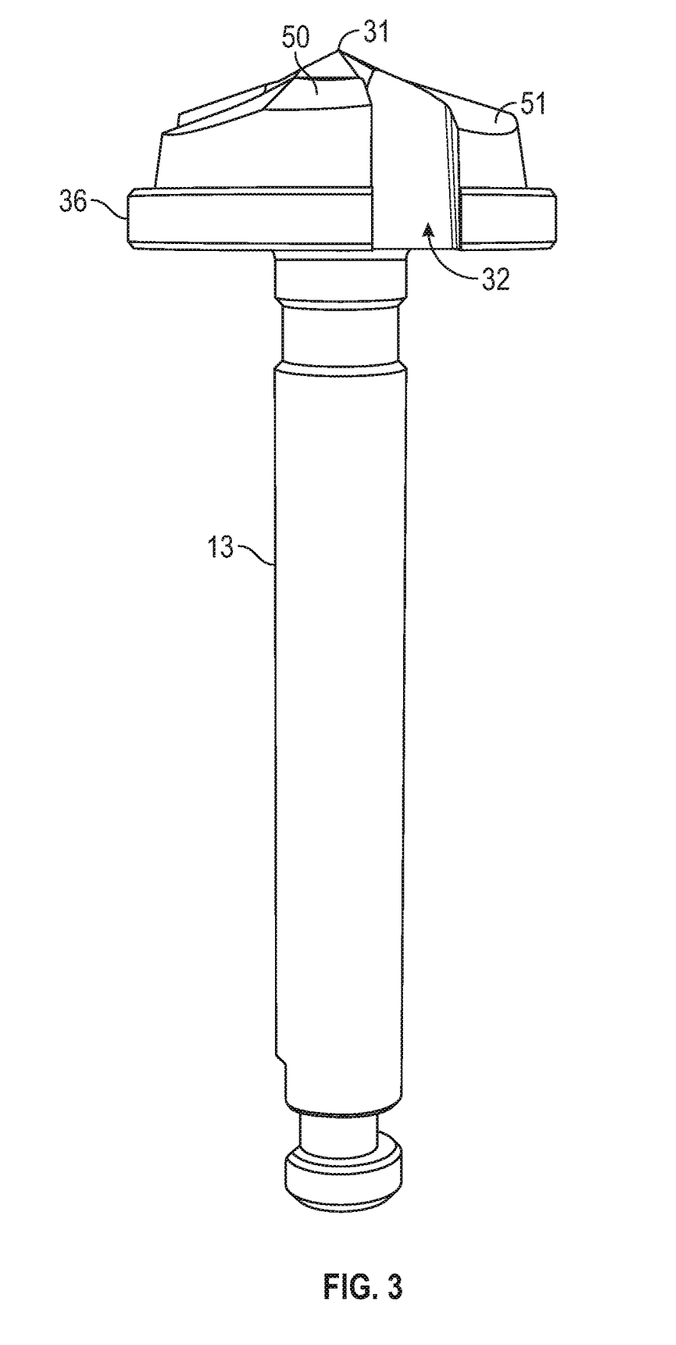
FIG. 3 illustrates a side view of a drill bit in FIG. 1 rotated about the longitudinal axis.
Figure 4:
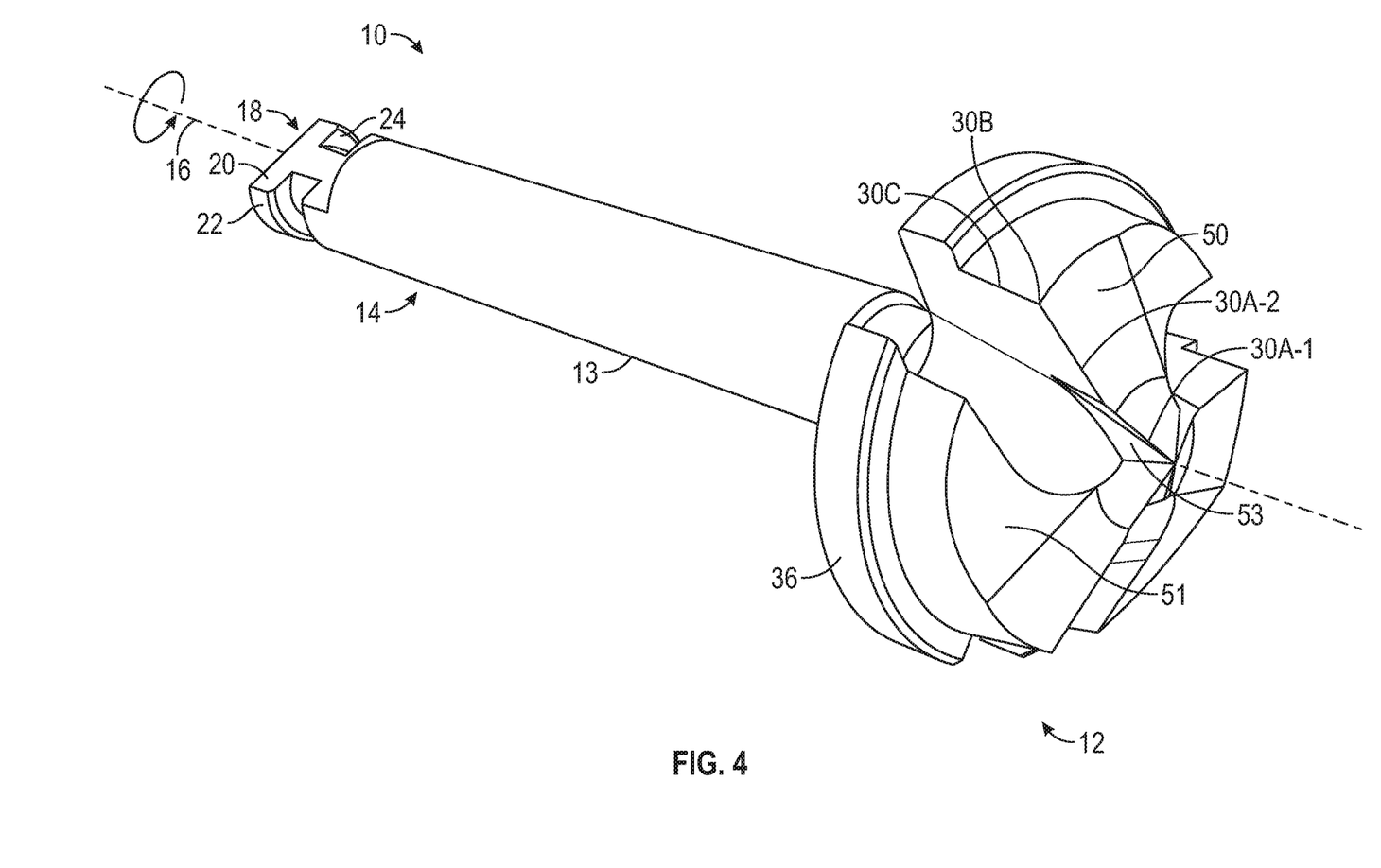
FIG. 4 illustrates a perspective view of the drill bit, according to one example of the present disclosure.
Figure 5:
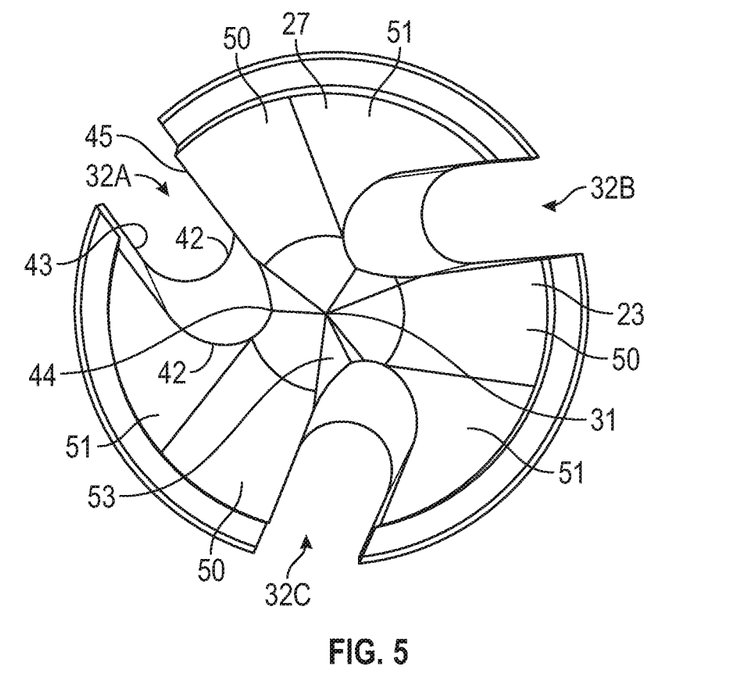
FIG. 5 illustrates a top down view of the drill bit, according to one example of the present disclosure.
Figure 6:
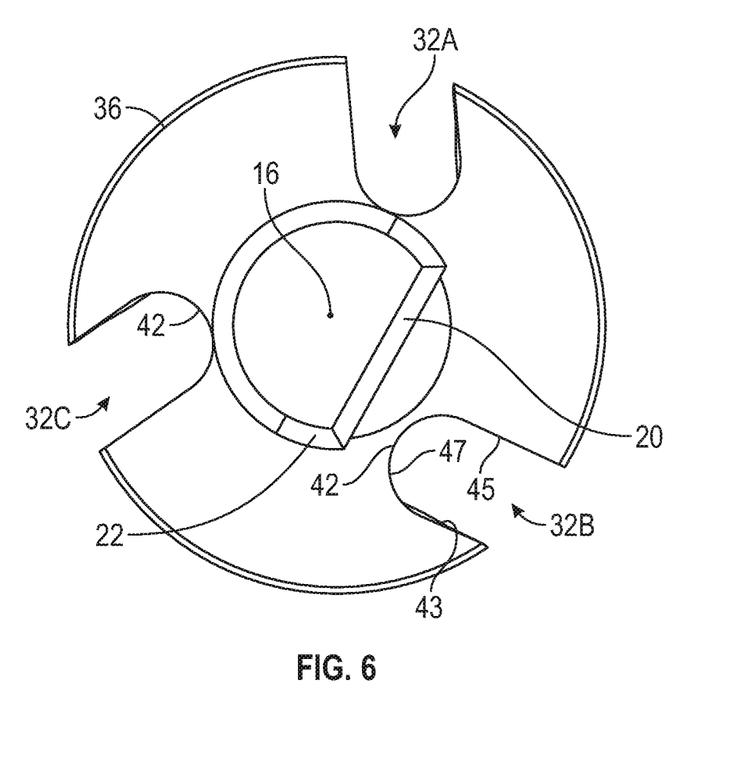
FIG. 6 illustrates a bottom view of the drill bit, according to one example of the present disclosure.

FIGS. 1-8 illustrate examples of the drill bit 10. FIG. 1 illustrates a side view of a drill bit 10, FIG. 2 illustrates a side view of the drill bit 10 rotated about a longitudinal axis compared to FIG. 1, FIG. 3 illustrates a side view of the drill bit 10 rotated about the longitudinal axis compared to FIG. 2, FIG. 4 illustrates a perspective view of the drill bit 10, FIG. 5 illustrates a top down view of the drill bit 10, FIG. 6 illustrates a bottom view of the drill bit 10, and FIGS. 7A and 7B illustrate a side view of a portion of the drill bit 10.

The drill bit 10 includes a mounting portion 12 and a working portion 14. The drill bit 10 can be mounted to a drill (or a hand-piece) to rotate the drill bit to drill bone in a patient's mouth. The mounting portion 12 includes a shaft 13 extending from a distal end 15 to a proximal end 17. The proximal end 17 can include a chuck 18 having a size and shape configured to be mounted to a hand-piece or drill. The chuck 18 can have a substantially "D" shaped cross section (see FIG. 6), and also has a substantially "I" shaped flat side 20 (see FIGS. 4 and 6). A semi-circle shaped disk 22 and a semi-circle shaped groove 24 can be formed by the "I" shaped flat side 20. The remaining shaft 13 of the mounting portion 12 can have a cylindrical shape. The diameter and shape of the shaft 13 can vary.

The working portion 14 is applied to cut or remove bones. The working portion 14 includes a body portion 23 having a top surface 27 and a side surface 25. As discussed herein, the working portion 14 includes a plurality of cutting blade portions 30A, 30B, 30C (collectively referred to herein as "cutting blade portion 30") for gradually cutting the surface and the inner wall of the bones and at least one channel 32 for storing the cut bones and discharging the cut bones. In one example, the working portion 14 includes a blocking portion 36 having a diameter that is greater than a maximum diameter of the body portion 23. The body portion 23 extends from a merge point 31 located on a longitudinal axis 16 of the drill bit 10 to a proximal end 34 of the body portion 23 that is adjacent to the blocking portion 36. As discussed herein, the blocking portion 36 can act as a stop and stop the drilling at a predetermined depth. The blocking portion 36 can define a shoulder 38 and an opposing bottom surface 40. The shoulder 38, having a diameter greater than a maximum diameter of the body portion 23, allows the shoulder 38 to contact a portion of the bone surrounding the opening and stop the drill bit 10 from advancing further.

The working portion 14 includes at least one channel 32 that can temporarily store bone chips produced from the drill bit 10 and can discharge the bone chips created while drilling from the drill bit 10. As seen in FIGS. 5 and 6, the drill bit 10 includes three channels 32A, 32B, 32C (collectively referred to as "channel 32" or "channels 32") that are spaced about 120 degrees in the circumferential direction. However, the number of channels 32 can vary. In on example, regardless of the number of channels 32 the spacing between adjacent channels 32 can be equal. In other examples, the spacing can be unequal between adjacent channels 32.

As seen in FIG. 6, the channels 32 along the bottom surface 40 include two side surfaces 43, 45 and a curved connecting surface 47. In one example, the two side surfaces 43, 45 can be parallel to each other. In other embodiments, they may not be parallel to each other. Each channel 32 has a point 42 along the curved connecting surface 47 that is closest to the longitudinal axis, however, the point 42 does not intersect the longitudinal axis 16. Each channel 32 defines a respective cutting blade portion 30.

The top surface 27 along the channel 32 can define the cutting blade portion 30A, which includes a first top cutting surface 30A-1 and a second top cutting surface 30A-2. Further, the top surface 27 includes a working top surface 50 and a trailing top surface 51. As seen in FIG. 5, the first and second top cutting surfaces 30A-1 and 30A-2 are defined between the channel 32 and the working surface 50. The shape of the channels 32 can vary depending on the location and type of drilling. As seen in FIG. 5, the side surfaces 43, 45 extend up from the bottom surface 40 to the top surface 27. The curved connecting surface 47 extends up to the top surface 27, but in this example, the point 42 along the curved connecting surface 47 closest to the longitudinal axis 16, is closer to the longitudinal axis 16 compared to the point 42 along the curved connecting surface 47 at the bottom surface 40.

Figure 7A:
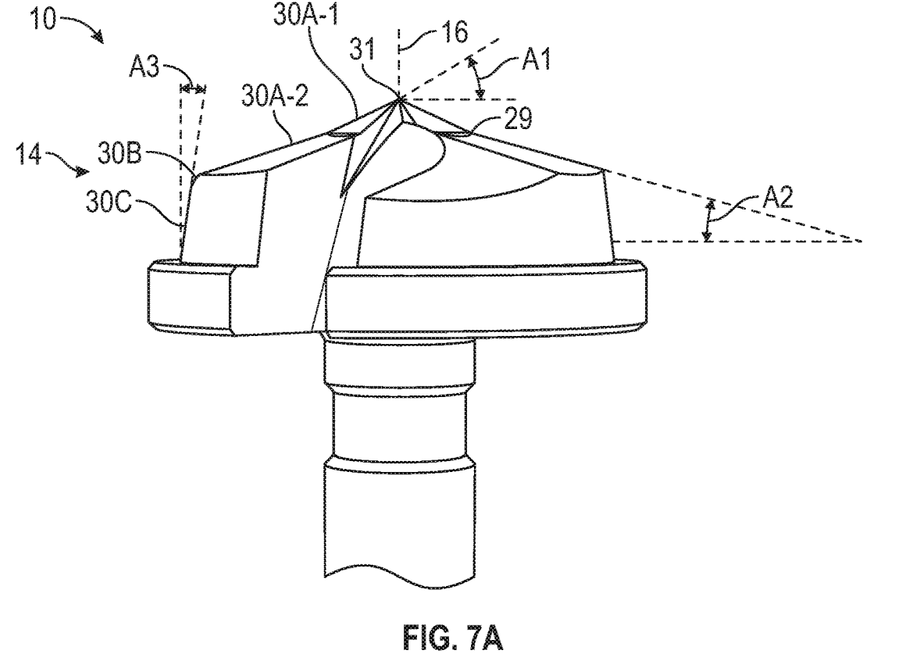
FIG. 7A illustrates a side view of a portion of the drill bit, according to one example of the present disclosure.
Figure 7B:
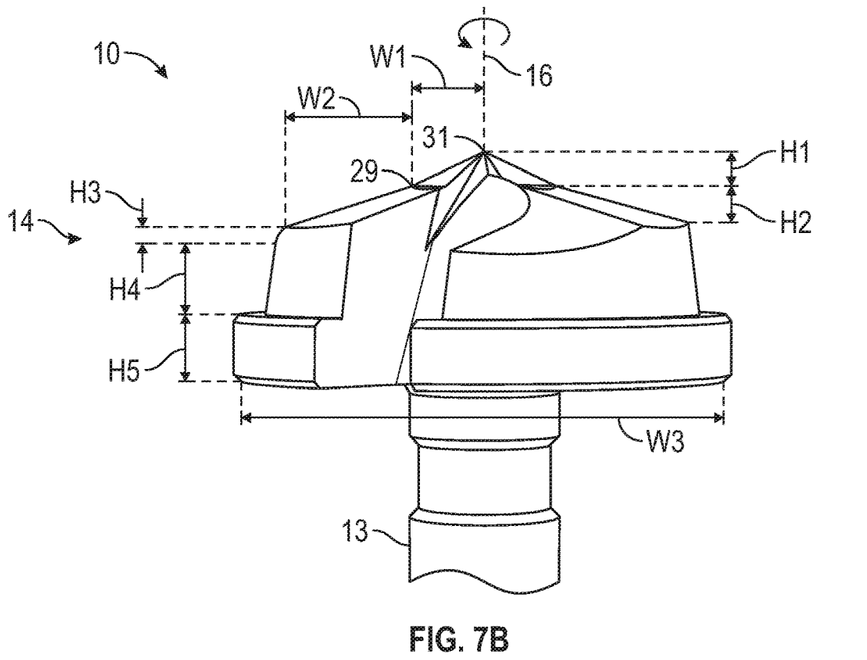
FIG. 7B illustrates the side view of a portion of the drill bit, according to one example of the present disclosure.

Referring to FIGS. 7A and 7B, further details of the working portion 14 of the drill bit 10 are disclosed. As discussed herein, the angles A1, A2 and axial height H1, H2 of the first and second top cutting surfaces 30A-1 and 30A-2 provide enough sharpness to initiate the cut without being so sharp to puncture membranous lining or soft tissues adjacent to the bone being drilled. The first top cutting surface 30A-1 is followed by a shallower tip (the second top cutting surface 30A-2). The second top cutting surface 30A-2 cuts the bone while spreading the axial force of the drill bit 10 as it impacts on the membrane or soft tissue. The first and second top cutting surfaces 30A-1, 30A-2 jointly combine to create the end cutting blades 30 with a total axial height (H1+H2) of about 1.0 millimeter (mm). In on example, the axial height of the first and second top cutting surfaces 30A-1 and 30A-2 can be within the range of about 0.5 mm to about 2.0 mm. Spreading out the axial force of the drill helps reduce the pressure of the first cutting surface 30A-1 on the membrane or soft tissue, reducing the likelihood of perforation. The channels 32 allow the particulate (bone chips) from the drilling action to have an escape path away from the membrane that will further prevent stress on the membranes or soft tissues. Any bone chips collected from the drilling process can also be used at autograft for the surgical procedure. As discussed herein, bone plates do not always form when drilling and can depend on various factors including the shape of the bone at the drilling location. The drill bit 10 disclosed herein is such that regardless of whether a bone plate is formed during drilling the risk of puncturing the membrane or tissue is reduced.

The cutting blade portions 30A-1, 30A-2, 30B, and 30C of the end cutting blades 30 are illustrated in FIGS. 7A and 7B. As discussed herein, the first top cutting surface 30A-1 includes an angle A1 relative to a line perpendicular to the longitudinal axis 16 that is greater than the angle A2 of the second top cutting surface 30A-2 relative to a line perpendicular to the longitudinal axis 16. As seen in FIGS. 7A and 7B, the first cutting blade portions 30A-1 merge at one merging point 31 on the longitudinal axis 16. The merging point 31 is formed from the first top cutting surfaces 30A-1 as a tip, where the first top cutting surface 30A-1 has angle A1 that is greater than angle A1 of the second cutting surface 30A-B.

The angle A1 of the first top cutting surface 30A-1 with respect to the line perpendicular to the longitudinal axis can be in the range of about 15 degrees to about 45 degrees. In one example, angle A1 can be within the range of about 20 degrees to about 30 degrees. In one example, angle A1 is about 25 degrees. If angle A1 is too steep (e.g., greater than 45 degrees), the risk of perforating a membrane or soft tissue increases however if angle A1 is too small (e.g., less than 15 degrees), the first top cutting surface 30A-1 is not sufficient to act as a pilot drill and the drill bit can "walk" on the bone before sufficiently engaging the bone to start drilling. Additionally, needing a separate drill to start the drilling and create a pilot hole will increase the time to complete the procedure.

The angle A2 of the second top cutting surface 30A-2 with respect to the line perpendicular to the longitudinal axis 16 is less than the angle A1. In an example, angle A2 can be in the range of about 10 degrees to about 25 degrees. In one example, angle A2 can be within the range of about 10 degrees to about 20 degrees. In one example, angle A2 is about 15 degrees. If angle A2 is too steep (e.g., greater than 25 degrees), the axial force of the drill with not be sufficiently spread such that the risk of perforating a membrane or soft tissue increases.

If angle A2 is too small (e.g., less than 10 degrees), the secondary to cutting surface 30A-2 can become an efficient cutting surface. However, in one example, angle A2 can be within the range of about 5 degrees to about 10 degrees when the angle A1 is greater than 25 degrees. If the angle A2 is shallower (less than 10 degrees), the angle A1 should be greater to offset the less efficient cutting of the second top cutting surfaces having the angle A2.

In one example, the height H1 of the first top cutting surface 30A-1 and the height H2 of the second top cutting surface 30A-2 can equal about 1 mm. However, other total heights can be used and can depend on the bone being drilled and other factors. In one example, H1 can be equal to or less than H2. That is, the first top cutting surface 30A-1 can be 50 percent (%) or less than the total height (H1+H2).

Additionally, other total height (H1+H2) configurations are possible. For example, any combined height of H1 and H2 could be possible provided the angles A1 and A2 stay in the described ranges, and as long as H1 remains smaller than H2. By having H1 equal to or smaller H2, the membrane or soft tissue is supported in a way that can minimize rupture or damage to the membrane or soft tissue. The drill bit 10 provided herein reduces the probability of puncturing membranes or damaging tissue and allow for the drilling of larger and smaller holes.

If the height H1 of the first top cutting surface 30A-1 is too long, the first top cutting surface 30A-1 (tip) will increase the risk of puncturing the membrane or soft tissue because the membrane or soft tissue isn't receiving support from the second top cutting surface 30A-2. If the height H1 of the first top cutting surface 30A-2 is too short, then the first top cutting surface 30A-1 will not act as a pilot drill, and it will be difficult to accurately start the hole without using an additional/separate pilot drill.

If the height H2 of the second top cutting surface 30A-2 is too short, then the second top cutting surface 30A-2 won't provide enough support to the membrane or soft tissue and the risk of the first top cutting surface 30A-1 puncturing the membrane increases. If the second top cutting surface 30A-2 is too long, then the drill bit 10 will be too wide and will cut away too big of a hole to be easily healed.

Since the angle A2 is less than A1, the width W2 of the second top cutting surface 30A-2, along a line perpendicular to the longitudinal axis 16, is greater than the width W1 of the first top cutting surface 30A-1, when H1 equals H2. However, the ranges for W1 and W2 are controlled by the angle A1, A2 and height H1, H2 ranges disclosed herein.

Figure 8:
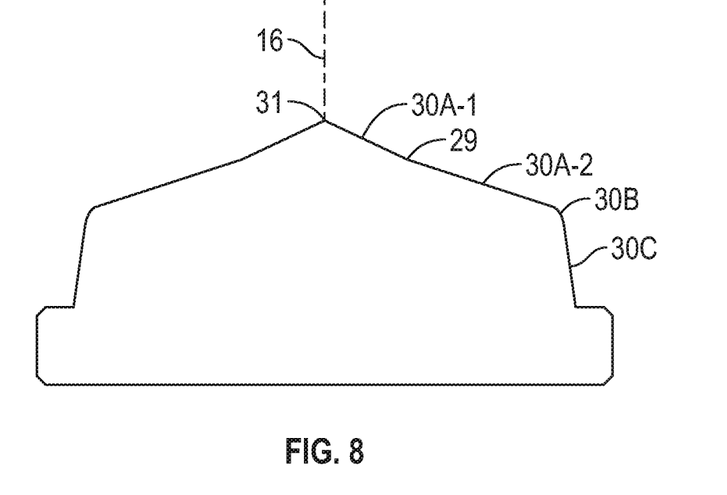
FIG. 8 illustrates a profile of a portion of a drill bit, according to one example of the present disclosure.

FIG. 8 illustrates a profile of an example of the top cutting surface 30A as the top cutting surface 30A transitions from the first top cutting surface 30A-1 to the second top cutting surface 30A-2. This transition can be done at a transition point 29 along the profile. As discussed herein, the transition point 29 can be about halfway between the total height (H1+H2) of the first and second top cutting surface combined. However, other locations for the transition point 29 are contemplated and can be based on a variety of factors.

The cutting blade portion 30 can include a side cutting edge 30C that can cut the side wall of the bones. The side cutting edge 30C is formed to outwardly have an angle A3 of about 0 degrees to about 25 degrees. In one example, angle A3 can be within the range of about 5 degrees to about 10 degrees. In one example, angle A3 is about 8 degrees. At 0 degrees, the side cutting edge 30C can still cut the bone due to the radial movement of the drill bit 10 by the tool rotating the drill bit 10. At greater than 25 degrees, the drilled hole becomes more of a cone, and the narrow ridges at the far end of the bone thickness are at risk of breaking off during the procedure. Broken bone tends to have jagged edges which can perforate the membrane. Additionally, wider angles require more bone area to be exposed at the proximal side of the bone.

Further, the height of the side cutting edges 30C can be between about 0.5 mm to about 5.0 mm. In one example, the height of the side cutting edges 30C can be between 0.5 and 3.0 mm. In one example, the height of the side cutting edges 30C is about 0.85 mm. Additionally, a set of drill bits 10 having a variety of diameters and lengths can be used such that the set of drill bits can be used in a variety of anatomies (different thickness and sizes of bones). A surgeon would prefer to have a family of drills with a variety of diameters and lengths to use in a variety of anatomies (different thickness and sizes of bones).

The cutting blade portion 30 further includes cutting corners 30B between the second top cutting surface 30A-2 and the side cutting edges 30C. In on example, the cutting corners 30B can be roundly formed to have a radius of curvature between about 0.4 mm to about 0.6 mm or a shape that can enable the drill to easily proceed from using the second top cutting surface 30A-2 to the side cutting edges 30C. Additionally, having round corners can also reduce the stress concentrations in the membranes or soft tissue. The membrane or soft tissue can wrap around the drill bit 10 along the cutting corners 30B during drilling and having sharp edges can increase the risk of punctures or damage.

Shown in FIGS. 2, 4, 5, 7A and 7B a relief 53 may be provided along the first top cutting surface 30A-1 and extend below a distal end of the second top cutting surface 30A-2. The relief 53 can be formed due to ease in manufacturing and allows the tip to cut easily as well as provides a channel for the bone chips to flow down into the channel 32 and toward the shaft of the drill bit 10.

Figure 9:
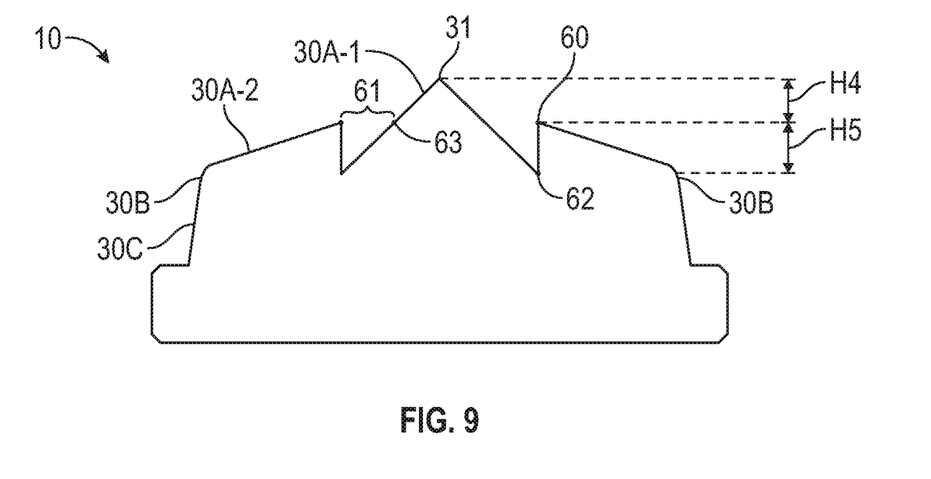
FIG. 9 illustrates a cross-sectional view of a portion of a drill bit, according to one example of the present disclosure.

FIG. 9 illustrates a cross-section of another example drill bit 10. In this example, the first top cutting surface 30A-1 extends from the merge point 31 to a proximal end 62 and the second top cutting surface 30A-2 extends from a distal end 60 to the side cutting edge 30B. As seen in FIG. 9, the distal end 60 of the second top cutting surface 30A-2 is positioned distally (above) the proximal end 62 of the first top cutting surface 30A-1. However, even in this example, the overall profile would have a transition point; however, the transition point in this example can be a transition surface 60 that is perpendicular to the longitudinal axis 16. The transitional surface 61 along the profile would be a distance from the proximal end 62 to a point 63 along the first top cutting surface 30A-1. In a profile view of the embodiment shown in FIG. 9, the transition surface 61 is between the second top cutting surface 30A-2 and the first top cutting surface 30A-1. Thus, in one example, the first top cutting surface 30A-1 can be recessed compared to the second top cutting surface 30A-2.

During use, the channels 32 of the drill bit 10 are empty before the bones are drilled by the drill bit 10. When the bones begin to be drilled by the drill bit 10, the channels 32 begin to be filled with the bone chips cut by the drill bit 10. The bone chips can escape from the channels 32 by the proceeding force of the drill bit 10 when uncut bones are met with the drill bit 10. However, even if there are no bone chips that form a bone plate, the shape of the drill bit 10 is such that stress concentrations are minimized in the membrane that would otherwise cause it to rupture. As discussed herein, bone plate formation during drilling (which can help protect the membrane or soft tissue) doesn't always occur and can depend on the anatomy of the patient and location of the drilling. For example, bone plate formation when drilling adjacent to the sinus membrane in the maxilla bone is highly variable. The drill bit 10 disclosed herein is shaped such that the risk of rupture of the membrane is reduced regardless if the bone plate is formed or not.

Figure 10A:
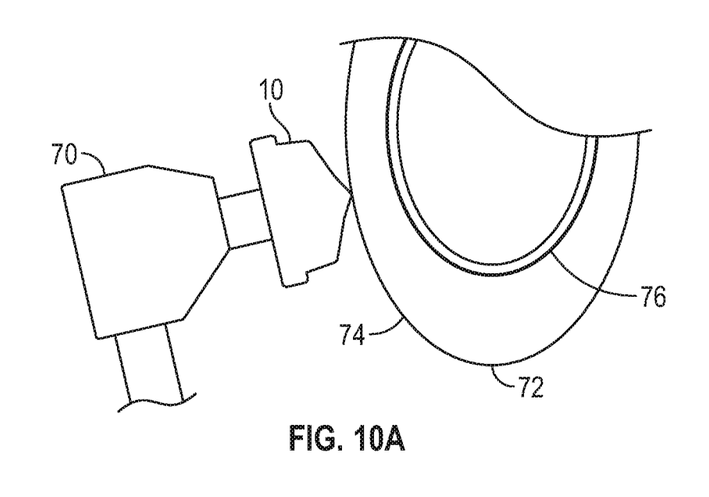
FIG. 10A illustrates a patient's jaw before drilling with the drill bit, according to one example of the present disclosure.
Figure 10B:
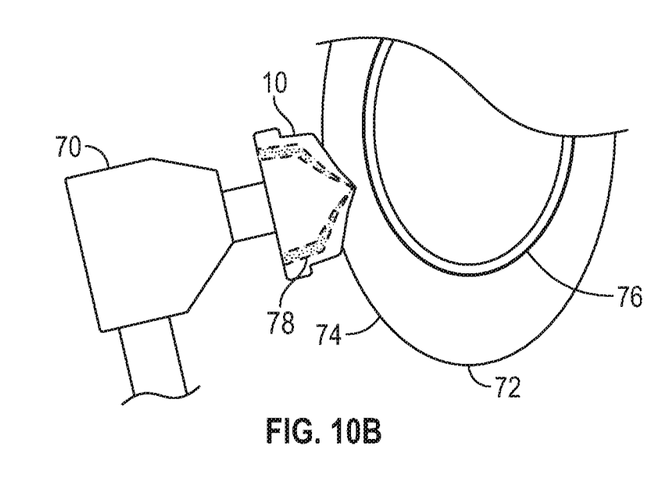
FIG. 10B illustrates the patient's jaw in FIG. 10A during drilling with the drill bit.

FIGS. 10A-10D illustrate the drill bit 10 being used to drill a hole into a tooth 72 using a tool 70 to rotate the drill bit 10. The tooth 72 includes bone 74 and adjacent to the bone 74 is a sinus membrane 76. FIG. 10A illustrates the drill approaching the tooth 72 and starting to drill. As discussed herein, the first top cutting surface is designed such that the first top cutting surface can act as a pilot drill and start the drilling while minimizing the drill walking along a surface of the tooth 72 while also reducing the risk of perforating the sinus membrane 76. FIG. 10B illustrates when the bones 74 begin to be drilled by the drill bit 10. As discussed herein, the channels 32 can begin to be filled with bone chips 78 cut by the drill bit 10, and any agglomerated bone chips 78 can be backwardly retreated from the channels 32 by the proceeding force of the drill bit 10 when they meet uncut bones.

Figure 10C:
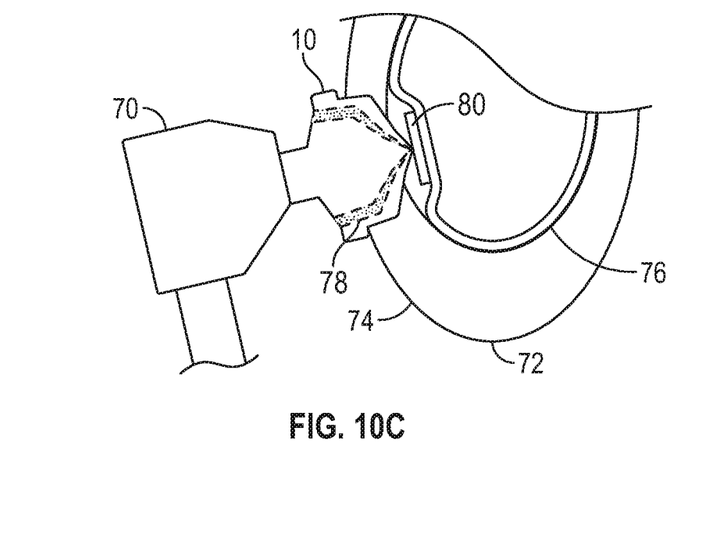
FIG. 10C illustrates the patient's jaw in FIGS. 10A and 10B once drilling with the drill bit is complete, according to one example of the present disclosure.
Figure 10D:
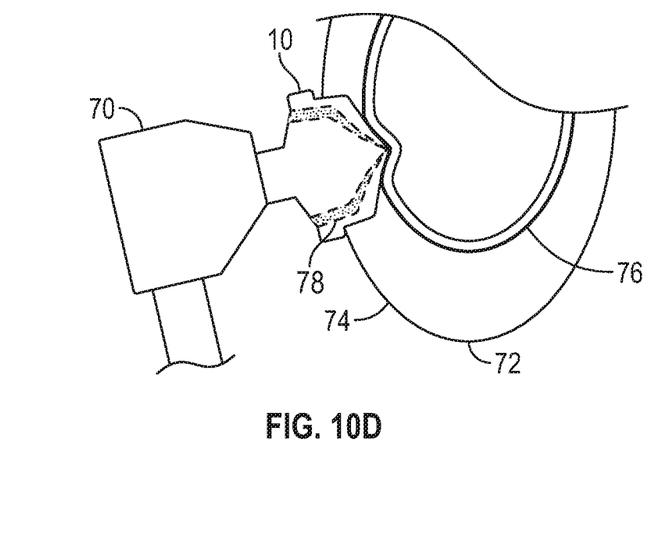
FIG. 10D illustrates the patient's jaw in FIGS. 10A and 10B once drilling with the drill bit is complete and no bone plate has been formed, according to one example of the present disclosure.

As shown in FIG. 10C, when drill bit 10 is close to the inner wall of the bones 74, the proceeding force of the drill bit 10 is greater than the resisting force of the inner wall and then the bones can be broken into a bone disk 80. Thus, in one example, the sinus membrane 76 can contact either the bone disk 80 or the agglomerated bone chips 78 located within the channels of the drill bit 10 and the sinus membrane 76 is not damaged. However, as discussed herein, bone chips may not properly agglomerate and bone disks may not be formed. As shown in FIG. 10D, the drill bit 10 has drilled through the sinus membrane 76 without forming a bone disk and the sinus membrane 76 is supported on the drill and is not perforated. Thus, the drill bit 10 of the present disclosure is such that even if no bone chips 78 agglomerate or the bone plate 80 (FIG. 10C) is not formed, the drill bit 10 will reduce the risk of puncturing the sinus membrane 76 or other soft tissue.

The present invention is not limited to the described embodiments. Instead, it would be appreciated by those skilled in the art that changes may be made to these embodiments without departing from the principles and spirit of the invention, the scope of which is defined by the claims and their equivalents.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" should be interpreted to include not just 0.1% to 5%, inclusive, but also the individual values (e.g., 1%, 2%, 3%, and 4%) and the sub-ranges (e.g., 0.1% to 0.5%, 1.1% to 2.2%, 3.3% to 4.4%) within the indicated range.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A surgical drill bit, comprising:
    a mounting portion extending from a first end to a second end, the mounting portion configured to mount to a tool; and
    a working portion adjacent the first end of the mounting portion, the working portion configured for cutting a hole in a bone, the working portion including:
        a body portion extending from a distal end to a proximal end, the body portion including a top surface and a side surface;
        a blocker formed at the proximal end of the body portion and having a first diameter greater than a maximum diameter of the body portion;
        at least one channel formed in a longitudinal direction of the working portion, the at least one channel extending from the top surface through the blocker,
    wherein the at least one channel defines, along the body portion, a cutting blade portion configured to cut the bone upon rotation of the surgical drill bit, the cutting blade portion including:
        a first top cutting surface having a first angle relative a longitudinal axis of the body portion; and
        a second top cutting surface having a second angle relative the longitudinal axis, the second angle less than the first angle.

2. The surgical drill bit of claim 1, wherein the first angle is between 15 degrees to 45 degrees with respect to a line perpendicular to the longitudinal axis.

3. The surgical drill bit of claim 1, the first angle is 25 degrees with respect to a line perpendicular to the longitudinal axis.

4. The surgical drill bit of claim 1, wherein the second angle is between 10 degrees to 25 degrees with respect to a line perpendicular to the longitudinal axis.

5. The surgical drill bit of claim 1, wherein the second angle is 25 degrees with respect to a line perpendicular to the longitudinal axis.

6. The surgical drill bit of claim 1, wherein the at least one channel is a plurality of channels each defining, along the body portion, the cutting blade portion.

7. The surgical drill bit of claim 6, wherein the cutting blade portion of each channel of the plurality of channels meet at a merging point on the longitudinal axis.

8. The surgical drill bit of claim 1, wherein along a profile of the working portion, the first top cutting surface changes to the second top cutting surface at a transition point.

9. The surgical drill bit of claim 8, wherein the transition point is halfway between a total height along the profile of the first top cutting surface and the second top cutting surface.

10. The surgical drill bit of claim 1, wherein the first top cutting surface extends from a merging point to a proximal end of the first top cutting surface, wherein the second top cutting surface extends from a distal end of the second top cutting surface to a cutting corner, and wherein the proximal end of the first top cutting surface is positioned proximally to the distal end of the second top cutting surface.

11. A surgical drill bit, comprising:
    a mounting portion extending from a first end to a second end, the mounting portion configured to mount to a tool; and
    a working portion adjacent the first end of the mounting portion, the working portion configured for cutting a hole in a bone, the working portion including:
        a body portion extending from a distal end to a proximal end, the body portion including a top surface and a side surface; and
        at least one channel extending through the body portion, wherein the at least one channel defines, along the body portion, a cutting blade portion, including:
            a first top cutting surface having a first angle relative a longitudinal axis of the body portion; and
            a second top cutting surface having a second angle relative the longitudinal axis that is greater than 10 degrees with respect to a line perpendicular to the longitudinal axis of the body portion, wherein the second angle is less than the first angle.

12. The surgical drill bit of claim 11, wherein a total axial height of the first top cutting surface and the second top cutting surface is 1.0 millimeter (mm).

13. The surgical drill bit of claim 11, wherein a height of the first top cutting surface is one of:
    equal to a height of the second top cutting surface and less than the height of the second top cutting surface.

14. The surgical drill bit of claim 11, wherein the first angle is between 15 degrees to 45 degrees with respect to a line perpendicular to the longitudinal axis.

15. The surgical drill bit of claim 11, wherein the second angle is between 10 degrees to 25 degrees with respect to the line perpendicular to the longitudinal axis.

16. The surgical drill bit of claim 11, wherein the at least one channel is a plurality of channels each defining, along the body portion, the cutting blade portion.

17. The surgical drill bit of claim 16, wherein the cutting blade portion of each channel of the plurality of channels meet at a merging point on the longitudinal axis.

18. A surgical drill bit, comprising:
    a mounting portion extending from a first end to a second end, the mounting portion configured to mount to a tool; and
    a working portion adjacent the first end of the mounting portion, the working portion configured for cutting a hole in a bone, the working portion including:
        a body portion extending from a distal end to a proximal end, the body portion including a top surface and a side surface; and
        at least one channel extending through the body portion, wherein the at least one channel defines, along the body portion, a cutting blade portion, including:

a first top cutting surface having a first angle relative a longitudinal axis of the body portion; and a second top cutting surface having a second angle relative the longitudinal axis, the second angle less than the first angle, wherein an axial height of the first top cutting surface is equal to or less than an axial height of the second top cutting surface.

19. The surgical drill bit of claim 18, wherein the first angle is between 15 degrees to 45 degrees with respect to a line perpendicular to the longitudinal axis.

20. The surgical drill bit of claim 19, wherein the second angle is between 10 degrees to 25 degrees with respect to the line perpendicular to the longitudinal axis.

* * * * *